United States Patent [19]

Lebowitz et al.

[11] 4,191,700

[45] Mar. 4, 1980

[54] SYNTHETIC LIQUID FUELS

[75] Inventors: Howard E. Lebowitz, San Jose; Ronald H. Wolk, San Jose; Seymour B. Alpert, Los Altos; Norman C. Stewart, San Jose; William C. Rovesti, Sunnyvale, all of Calif.

[73] Assignee: Electric Power Research Institute, Inc., Ralo Alto, Calif.

[21] Appl. No.: 930,266

[22] Filed: Aug. 2, 1978

Related U.S. Application Data

[63] Continuation-in-part of Ser. No. 799,831, May 23, 1977, abandoned.

[51] Int. Cl.$^2$ .................. C07C 1/04; C07C 31/06
[52] U.S. Cl. .................. 260/449 M; 260/449.6 M; 260/449.5; 208/8 LE; 208/10; 252/373; 48/197 R
[58] Field of Search .................. 260/449 M, 449.6 M, 260/449.5, 449 L; 208/8 LE, 8 R, 10; 252/373; 48/197

[56] References Cited

U.S. PATENT DOCUMENTS

| | | | |
|---|---|---|---|
| 3,528,930 | 9/1970 | Schlinger | 252/373 |
| 3,536,608 | 10/1970 | Riedl et al. | 208/8 |
| 3,700,584 | 10/1972 | Johanson et al. | 208/10 |
| 3,764,547 | 10/1973 | Schlinger et al. | 252/373 |
| 3,866,411 | 2/1975 | Marion et al. | 252/373 |
| 3,888,896 | 6/1975 | Espino et al. | 260/449.5 |
| 3,986,349 | 10/1976 | Egan | 260/449.6 R |
| 4,031,123 | 6/1977 | Espino et al. | 260/449.5 |
| 4,050,908 | 9/1977 | McNamee et al. | 260/449 M |

FOREIGN PATENT DOCUMENTS 1164407  9/1969  United Kingdom .................. 260/449.5

*Primary Examiner*—Howard T. Mars
*Attorney, Agent, or Firm*—Bertram I. Rowland

[57] ABSTRACT

An economical, efficient process is provided employing coal, particularly subbituminous coal, as a fuel source for the production of distillate fuels, methanol, and methane. A hydroliquefier is operated under severe conditions to provide a high net yield of light distillates which are separated by distillation. The vacuum residue, which is produced above, is transferred as a slurry to a partial oxidation gasifier where synthesis gas is produced as feedstock for methanol or methane synthesis. Gaseous hydrocarbon contaminants are separated and used to generate additional synthesis gas, or to supply other fuel requirements. No net heavy distillates are taken as a product, being used as a fuel or converted to other products.

8 Claims, 1 Drawing Figure

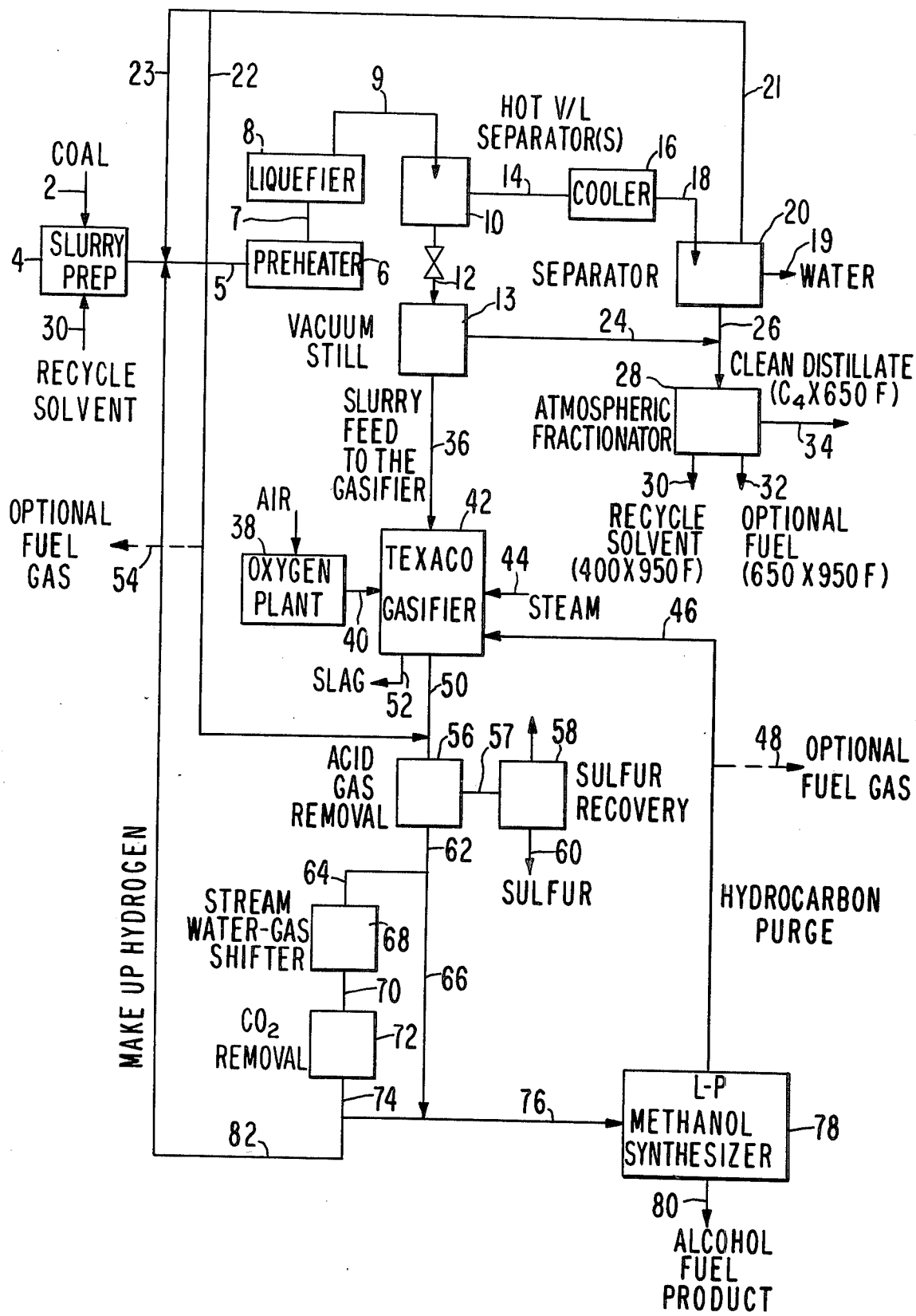

SYNTHETIC LIQUID FUELS

CROSS-REFERENCE TO RELATED APPLICATION

This application is a continuation-in-part of application Ser. No. 799,831, filed May 23, 1977 now abandoned.

This invention was made under contract with or supported by the Electric Power Research Institute, Inc. of Palo Alto, California.

BACKGROUND OF THE INVENTION

1. Field of the Invention

There is a continuing interest in the upgrading of fuels, particularly coal, to provide fuels having a wide variety of applications and coming within specified standards, such as environmental standards, physical standards, and the like. Because of the relatively large supplies of coal, much attention has been focused on the use of coal to replace oil. Bituminous and subbituminous coal has only limited utility as obtained from mining operation. The coal contains substantial amounts of sulfur, nitrogen and inorganic compounds such as calcium salts. In order to meet environmental standards, it is necessary to remove substantial amounts of the sulfur and nitrogen. Since calcium and other inorganics have no fuel value, they act to reduce the heat content per unit weight of coal and are contaminants which must be removed from a combustion zone. Furthermore they may interfere with the proper operation of the fuel combustion apparatus. In addition, in many generation operations it is desirous to have a liquid, rather than a solid fuel.

In any refining of coal to upgrade the coal to an acceptable fuel, it is essential that the system be economical and efficient and, whenever possible, provide at least a portion of the fuels necessary for the processing. In addition, it is desirable to produce products which have high economic value in comparison to the original coal value.

2. Description of the Prior Art

U.S. Pat. No. 3,888,896 describes a liquid phase methanol synthesis process. U.S. Pat. Nos. 3,816,322 and 3,764,547, and patents cited therein, describe a partial oxidation gasifier.

SUMMARY OF THE INVENTION

A process is provided for the economic and efficient upgrading of coal to a clean, light distillate fuel, a heavy distillate fuel and methanol or methane. Coal is solvent refined under severe conditions, preferably in a hydrogen environment, to provide a substantially liquid product, which is divided in a separation zone to a light distillate product, recycle solvent, a heavy distillate, and a vacuum residue slurry. The vacuum residue slurry provides an efficient feed for a partial oxidation gasifier which produces synthesis gas as a feed for methanol and/or methane production and to supply hydrogen, as required, to the above liquefier. Hydrocarbon contaminants in the synthesis gas feed are returned to the gasifier or otherwise processed for conversion to additional synthesis gas. The heavy distillate may be used for in-plant fuel requirements. Alternately, the hydrocarbon gases may be used for in-plant fuel and the heavy distillate gasified with the vacuum residue. The primary product is a high yield of a distillate boiling below about 650° F. ($-650°$ F.).

BRIEF DESCRIPTION OF THE DRAWING

The FIGURE is a diagrammatic view of a process according to the subject invention.

DESCRIPTION OF THE SPECIFIC EMBODIMENTS

The process of the subject invention is concerned with the efficient and economical production of light distillate and methanol or methane. Coal, particularly bituminous or subbituminous coal, and preferably the latter, is employed as the raw material.

In carrying out the process, a hydroliquefier is employed, whereby coal is contacted with hydrogen and recycle solvent under severe conditions to produce high yields of light distillate. The gaseous fraction is taken overhead, and hydrogen separated and recycled to the hydroliquefier. The liquid fraction is transferred to a separation zone and divided into a light distillate fraction, a heavy distillate fraction, and a vacuum residue slurry. The light distillate fraction is a clean fuel. The heavy distillate fraction may be employed within the plant as fuel, may be fed to the gasifier along with the vacuum bottoms, may be further hydrocracked into light distillates, or stored and used for other purposes, normally within the plant. The residue serves as a feed stock for a partial oxidation gasifier which provides the synthesis gas feed stock for methanol and/or methane production. Any hydrocarbon impurities recovered from the methanol production step may be separated and returned to the gasifier, used as a fuel gas, or steam-reformed to make additional synthesis gas.

The first stage of the process is the hydroliquefier. The hydroliquefier employs finely comminuted coal and hydrogen donor solvent as a feedstock. Various processes for liquefying coal may be found in a wide variety of patents. See for example U.S. Pat. Nos. 3,536,608 and 3,700,584.

In the subject invention, various bituminous coals may be employed, but subbituminous coal is preferred, because it provides a high yield of light distillate, which is low in sulfur and nitrogen. The comminuted coal will generally be less than about one-quarter inch in diameter, more usually less than one-eighth inch, and generally from about 20 to 200 Tyler mesh, more usually about 40 to 100 Tyler mesh. The size of the coal particles is not critical to this invention, and substantial variation is permitted.

The hydrogen donor solvent is primarily partially hydrogenated aromatic hydrocarbons. Mixtures of hydrocarbons are generally employed, usually boiling in the range of about 400° to 975° F. Examples of suitable solvent components are tetralin, decalin, biphenyl, methylnaphthalene, etc. Other types of solvents which may be added to the preferred solvents or may be present as part of the recycle stream include phenols such as phenol and cresol. The solvent may be hydrogen treated prior to introduction into the hydroliquefier to enhance the hydrogen donor capacity.

The operating conditions of the hydroliquefier are severe so as to enhance the production of light distillates. The liquefier will normally be operated at temperatures between about 800° F. and 900° F., more usually between about 800°–875° F. and at pressures from about 1000 to 4,000 psig, usually 1,500 to 3,000 psig. Reactor space rates will generally be in the range of 5 to 500 pounds of coal per hour per cubic foot of reactor volume, more usually 5 to 40 pounds of coal per hour per cubic foot of reactor volume. While in some instances, catalysts may be added, such as oxides or sulfides of nickel, molybdenum, cobalt, and the like, supported on a high surface area alumina or silica alumina base, normally the process will be noncatalytic.

The process may be carried out in the presence or absence of hydrogen, normally in the presence of hydrogen. Where hydrogen is employed, the amount of hydrogen will generally vary from about 5 to 50 scf per pound of coal.

The weight ratio of solvent to coal will generally be in the range of about 1 to 10:1, preferably 1-3:1, and particularly preferred 1.5-3:1.

The gas which exits from the hydroliquefier will be a mixture primarily of hydrogen sulfide, carbon dioxide, water, methane, and hydrogen. By employing conventional scrubbing techniques, the hydrogen can be purified free of the other gases and recycled to the hydroliquefier.

It is generally desirable that the liquefier be operated at an equal or greater pressure than the preferred pressure for operation of partial oxidation gasifiers.

The substantially liquid effluent from the hydroliquefier will be transferred to a separation zone, a distillation section, and preferably, one which includes a vacuum distillation column. The hydroliquefier effluent will be divided into four fractions, light distillate, recycle solvent, heavy distillate, and vacuum bottoms. Preferably, the separation is carried out in two stages, where the distillate is divided into two fractions, the first fraction boiling up to 650° F. and the second fraction boiling between 650° F. and 975° F. The lower boiling fraction is then further separated into recycle solvent and light distillate i.e. $C_4 \times 400°$ F. and 400° to 650° F. The quantity of vacuum bottoms will be such that when gasified, as described below, will supply a substantial excess of gas over that which is required for the manufacture of make up hydrogen for the liquefier.

Based on the coal (dry ash-free basis), the yield of light distillate will be in the range of about 15 to 45 weight percent, usually in the range of about 17 to 40 weight percent, and the stream of vacuum bottoms will be in the range of about 40 to 80 weight percent, usually in the range of about 44 to 75 weight percent.

Without any further processing, the residue from the separation zone is employed as a feedstock for a partial oxidation gasifier. This type of gasifier which produces synthesis gas has been described extensively in the patent literature. Various special techniques may be employed as described in U.S. Pat. Nos. 3,528,930 3,816,332 and patents cited therein. Therefore, only a brief description of the process will be provided.

The residue, containing ash, is fed to the partial oxidizer and reacted with oxygen and steam in a closed reaction zone at an autogeneous temperature within a range of about 1,800° F. to 3,000° F., usually about 2,200° F. to 2,800° F. The residue and steam are generally preheated to about 500° F., usually at least 600° F. The reactor zone pressure is generally about 300 to 1,000 psig, although higher pressures are possible.

The products from the gasifier are carbon monoxide and hydrogen, containing small amounts of carbon dioxide, methane and entrained carbon. The entrained carbon may be removed by conventional methods and recycled to the gasifier. The gas stream is purified in conventional gas cleaning equipment from which it is transferred to a methanol or methane synthesizer.

The hydrogen-to-carbon monoxide ratio of the above gas will be shifted to increase the proportion of hydrogen. The means for doing this are conventional and will be apparent to one skilled in process engineering design. The acid gases will be removed.

In the shift process, the synthesis gas is contacted with water under conditions where carbon monoxide reacts with the water to produce hydrogen and carbon dioxide. The hydrogen rich stream is then split, a portion employed for make-up hydrogen for the liquefier and the remaining portion combined with the gasifier stream to provide at least the stoichiometric requirements for methanol or methane production, 2 and 3 molar proportion respectively.

While various processes for the synthesis of methanol may be employed, the preferred process is found in U.S. Pat. No. 3,888,896, which is illustrative of methanol production from synthesis gas. The specific process carries out the methanol synthesis in a liquid medium. Briefly, polyalkylbenzenes are used as a liquid medium and boil from about 100° C. to 250° C., although other liquids may also be included. The reaction temperature employed ranges from about 200° F. to 950° F., usually from about 400° F. to 750° F. with pressures from about 200 to 10,000 psia, usually from about 500 to 3,500 psia. Normally, hydrogen will be in excess of the stoichiometric requirements, usually not more than 5, more usually not more than 4 times stoichiometric. The flow rate of reactants will generally be from about 0.1 to 10 pounds of feed per pound of catalyst per hour more usually about 0.5 to 5 pounds of feed per pound of catalyst per hour.

Any conventional methanol forming catalyst may be employed, for example, a copper, chromium or zinc catalyst as described in U.S. Pat. No. 3,326,956.

The methanol stream which exits from the methanol synthesizer will generally be contaminated with low molecular weight volatile hydrocarbons. These may be readily separated from methanol and the hydrocarbons returned to the gasifier. Alternatively, where the stoichiometry does not provide for complete reduction of the carbon monoxide, the unconverted reactants in the exiting gas stream may be employed directly for generation of electric power or for fuel. Alternatively, a side stream may be taken from the gasifier effluent to be used for the direct generation of electric power. In addition, the hydrocarbon purge from the methanol unit may be steam reformed to make synthesis gas, which may then be cycled to the methanol synthesis unit, rather than recycling the hydrocarbon purge to the gasifier unit.

The methanol produced from excess gasification products will generally be in the range of about 35 to 80 percent, usually 40 to 60% of the total heating value of the fuel products.

In a further variation, the methanol synthesis unit may be replaced with a methane synthesis unit, so that methane rather than methanol is prepared, which may then be used as a fuel.

Methanation can be achieved by treating a synthesis gas having the appropriate stoichiometric ratio at temperatures in the range of about 900° to 1500° F. over a nickel, cobalt or iron catalyst on a support e.g. alumina. See U.S. Pat. Nos. 3,938,968 and 4,050,908.

For further understanding of the invention, the drawing will now be considered. (Temperature ranges are indicated as $A \times B$ or the initial or terminal temperature indicated by the hydrocarbon fraction e.g. C4 boiling at that temperature.)

Coal (2) and recycle solvent (30) are slurried together in slurry preparation section (4), the coal being relatively dry and in finely comminuted form. The slurry is mixed with fresh hydrogen (82) and recycle gas (23) at the preheater (6). The heated products (7) flow to the liquefier (8). The liquefier product (9) is separated into vapors (14) and liquids (12) in the hot vapor/liquid separator (10). The liquid product (12) is fed to a vacuum still (13). The vapor products (14) are cooled and flow in a separator (20) wherein the fixed gases (21) are separated from water (19) and condensed hydrocarbons (26).

The overhead products (24) from the vacuum still (13) are mixed with the condensed hydrocarbons (26) and these are fed to an atmospheric fractionation section (28). Up to three products are taken from the atmospheric fractionation, namely: $C_4 \times 400°$ F., $400° \times 650°$ F., and $650° \times 975°$ F. Part of the $400° \times 650°$ F. fraction and part of the $650° \times 975°$ F. fraction may be combined as the recycle solvent (30). The $C_4 \times 400°$ F. fraction and part of the $400° \times 650°$ F. comprise net clean distillate product (34). The balance of the heavy distillate, $650° \times 975°$ F. product (32) may be used as plant fuel. The optional heavy fuel (32) may be absent depending upon the desired product distribution. The vacuum still may be operated to leave this cut in the vacuum bottoms (i.e., slurry feed (36) to the gasifier (42)).

The overhead product (21) from the separator (20) is split partially into recycle gas (23) and purge gas (22). Stream (22), above, will be of such quantity to control the build up of impurities in the liquefier feed gas and provide the desired partial pressure of hydrogen in the liquefier. Stream (22) will contain hydrogen as well as hydrocarbon gases, carbon monoxide, carbon dioxide, hydrogen sulfide and other impurities. This stream may be admixed with the gasifier output (50) or may alternately be used as a source of fuel gas.

The vacuum bottoms product (36) and optionally purge gas stream (46) are fed to partial oxidation gasifiers (42) along with oxygen (40) and steam (44). Synthesis gas consisting principally of carbon monoxide, hydrogen and acid impurities ($CO_2$, $H_2S$, COS) is the product (50). The acid gas impurities are removed in section (56). It may optionally be desired to concurrently remove hydrocarbon impurities if a physical absorption system is used for acid gas removal. If this were done, part or all of stream (48) would be removed as a stream from block (56) rather than from the methanol synthesis purge (46). A portion of the clean gas stream (62) is shifted to form relatively pure hydrogen in blocks (68) and (72). An aliquot of the hydrogen (82) is returned to the coal liquefaction section. The remainder of the gas (66) is remixed with unshifted gas to form the methanol synthesis gas feed (76). The split between streams (62) and (64) is chosen to be such that stream (76) has a molar ratio of $H_2/CO$ being approximately equal to 2. The hydrogen and CO are converted to methanol in block (78) from which impurities emerge as stream (46) and alcohol product as stream (80).

While the figure indicates the formation of methanol, methane could equally be the product or a mixture of the two depending on the desired product mix. By shifting the clean gas stream to provide sufficient hydrogen to be mixed with the unshifted gas to have a mole ratio of $H_2:CO$ of 3:1, methane could be obtained in accordance with known conventional procedures.

In the above description, it should be understood that the key process steps have been described in their concept, and that one skilled in the engineering design of process plants would recognize engineering alternatives for carrying out the same process steps. In particular, it will be important to the overall economics of the process to efficiently recover energy (heat) from streams being cooled and to utilize this energy to offset other process requirements. The particular choice of such items will be apparent to one skilled in the art.

In the subject process, coal is transformed into a number of high quality fuels and chemicals by means of an economical and efficient process. Rather than using the coal directly in a gasifier to produce carbon monoxide and hydrogen, the process first hydroliquefies the coal under severe conditions, so as to give a high yield of an economically valuable light distillate fraction. In addition, the process provides hydrogen for the hydroliquefaction of coal and fuel for operation of the plant. The vacuum residua, which is a pumpable slurry at elevated temperature, is employed for the production of synthesis gas and ultimate production of methanol, or may be used as a fuel. Alternatively, the process can be easily modified to produce methane rather than methanol. A key feature of the process is the coproduction of distillates and methanol (or alternately methane) in significant high yields.

The process can easily accommodate an increased yield of methanol if this is desired. The slurry feed to the gasifier (36) is capable of accepting additional solid hydrocarbons, such as coal, while still maintaining its slurry character. A substantial quantity of coal, equal to 30% or more by weight of stream (36), may be added. This is demonstrated in Example 4, below.

The subject process demonstrates how the hydrogen and carbon values of coal can be upgraded to provide useful fuels and chemicals. The various products derivable from coal are integrated into a single system to produce a spectrum of products, which either may be used internally or provide high grade fuels or raw materials for further processing.

For purposes of illustration, the following examples demonstrate the operation and benefits of the subject invention.

EXAMPLE 1

Hydroliquefaction

Subbituminous coal (1) from the Wyodak Mine located in Campbell Country Wyoming (Wyodak-Anderson Seam) was liquefield in a continuous flow apparatus with conditions and yields as follows:

| Coal Analysis | |
|---|---|
| Moisture, W% | 6.4 |
| Proximate, W% (dry) | |
| Ash | 7.0 |
| Volatile Matter | 46.5 |
| Fixed Carbon | 46.5 |
| Ultimate, W% (dry) | |
| Carbon | 67.8 |
| Hydrogen | 5.0 |
| Nitrogen | 0.8 |
| Sulfur | 0.8 |
| Ash | 7.0 |
| Oxygen (by difference) | 18.6 |
| Heating Value (dry basis) | 11,480 Btu/pound. |

(1) Johanson, Edwin, *Solvent Refining of Wyodak, Illinois and Black Mesa Coals*, EPRI RP389 (vol. 2), Electric Power Reserach Institute, Palo Alto, Calif., February 1976 (Data quoted are Run 177-114)

| RUN NUMBER | 22 | 13B |
|---|---|---|
| Run Conditions | | |
| Coal Space Rate $\frac{\text{lb of dry coal}}{\text{hr} - \text{Ft}^3}$ | 32 | 32 |
| Recycle Solvent to Coal, wt ratio | 2 | 2 |
| Temperature, °F. | 840 | 835 |
| Pressure, psig (pure $H_2$ feed gas) | 2500 | 2000 |
| Type of reactor | Perfectly mixed flow | |
| Yields, Weight % of MAF[(1)]Coal | | |
| $CO_2$ | 8.25 | 5.84 |
| CO | .61 | 1.77 |
| $C_1 \times C_3$ | 9.10 | 5.70 |
| $C_4 \times 350°$ F. | 8.23 | 8.28 |
| $350 \times 650°$ F. | 11.53 | 8.81 |
| $650 \times 950°$ F. | 10.01 | 13.08 |
| + 950° F. Residuum Oil | 36.99 | 34.94 |
| MAF Unconverted Coal | 7.38 | 13.19 |
| $H_2O$ | 10.66 | 10.66 |
| $NH_3$ | .24 | .13 |
| $H_2S$ | .50 | .47 |
| Total (100 + Hydrogen reacted) | 103.50 | 102.87 |
| [(1)]Moisture and ash free. | | |
| Properties of Products, W% | | |
| $C_4 \times 350°$ F. | | |
| % Sulfur | 0.09 | — |
| % Nitrogen | 0.06 | — |
| $350 \times 650°$ F. | | |
| % Sulfur | 0.40 | — |
| % Nitrogen | 0.30 | — |

EXAMPLE 2

Gasification of Hydroliquefaction Vacuum Bottoms Slurry

Vacuum bottoms slurries from hydroliquefaction procesing Wyodak Coal (2) were gasified in a Texaco partial oxidation gasifier. Summarized results are as follows:

| Cold Gas Efficiency - 85% |
|---|
| (Gross heating value of the synthesis gas as a fraction of gross heating value of the feed) |
| SCF of Oxygen |
| Oxygen Consumption = $\frac{.270 \text{ SCF of } O_2}{\text{SCF of CO} + H_2}$ |

(2) Robin, Allen M., *Hydrogen Production from Coal Liquefaction Residue*, EPRI AF-233 Final Report, Electric Power Reserach Institute

EXAMPLE 3

Integration of Liquefaction and Gasification and Methanol Synthesis

Based on the above, Examples 1 and 2, the following yields are projected for their combination in accord with FIG. 1 (Run 22 of Example 1), wherein streams 48 and 54 are null.

Yields, per 100 Btu net (lower) heating value of coal.

| $C_4 \times 350°$ F. Distillate | 12.8 | Btu (LHV) |
|---|---|---|
| $350 \times 650°$ F. Distillate | 17.3 | Btu (LHV) |
| $650 \times 975°$ F. Distillate | 15.5 | Btu (LHV) |
| Methanol | 34.6 | Btu (LHV) |
| Total | 80.2 | |

| OXYGEN REQUIRED | 0.05 SCF |
|---|---|

For comparison, if methanol were produced from coal directly by partial oxidation, with feed in a water slurry, the products would be approximately 55 to 60 Btu of methanol (LHV) per 100 Btu of feed coal (LHV), and the oxygen consumption would be more than twice as high.

In both of the above cases, the internal plant fuel requirements have not been considered. The net plant fuel requirements are about equal for the two cases.

The advantages of the subject invention with regard to plant efficiency are thus readily apparent.

EXAMPLE 4

Addition of Coal to Vacuum Bottoms

The following data illustrates the fluidity of vacuum bottoms from processing of subbituminous coal and admixtures of that coal with the vacuum bottoms at 600° F.

Vacuum Bottoms—0.4 poise

30% Coal/70% Vacuum Bottoms—11.0 poise

Although the foregoing invention has been described in some detail by way of illustration and example for purposes of clarity of understanding, it will be obvious that certain changes and modifications may be practiced within the scope of the invention as limited only by the scope of the appended claims.

What is claimed is:

1. A highly efficient method of producing from coal liquid volatile products having fuel values which comprises:

(a) in a hydroliquefaction zone liquefying coal by contacting comminuted coal with hydrogen and a hydrogen donor recycle solvent boiling in the range of about 400°-975° F. under severe conditions comprising temperatures in the range of 800° to 900° F. and pressures in the range of 1,000 to 3,000 psig and a solvent to coal weight ratio of 1.5-3:1 to produce a high yield of light distillates boiling below about 650° F. said yield of light distillates comprising from about 15 to 45 weight percent of the coal (dry ash free basis), whereby a substantially gaseous effluent and a substantially liquid effluent are obtained;

(b) transferring said liquid effluent to a vacuum distillation separation zone and distilling said liquid effluent into a light distillate fraction, boiling below about 400° F., a middle distillate solvent fraction boiling between about 400° to 650° F., a heavy distillate fraction boiling between about 650° to 975° F., and vacuum bottoms slurry boiling above about 975° F., the quantity of which, when gasified, will supply substantially more gas than is required for producing hydrogen for the hydroliquefier;

(c) pumping said vacuum bottoms slurry into a partial oxidation gasifier and transforming said bottoms to synthesis gas consisting essentially of carbon monoxide and hydrogen;

(d) shifting the hydrogen to carbon monoxide ratio of the said synthesis gas to produce a hydrogen enriched gas and removing the acid gases therefrom;

(e) recycling a portion of said hydrogen enriched gas from said synthesis gas from step (d) to the hydroliquefier;

(f) reacting the remainder of said synthesis gas to produce methanol or methane;

(g) recycling at least a portion of said 400°–650° F. and said 650°–975° F. fractions in admixture as said recycle hydrogen donor solvent to said hydroliquefaction zone.

(h) utilizing excess of said 650°–975° F. as fuel for the plant.

(i) withdrawing the remainder of product boiling below about 650° F. not recycled in step (g).

2. A method according to claim 1 wherein the stream of vacuum bottoms comprises from about 40 to 80 weight percent of said coal, and where methanol is produced from excess gasification products and amounts to from about 35 to 80% of the total heating value of the fuel products.

3. A method according to claim 2 where the coal is subbituminous coal.

4. A method according to claim 3 wherein said heavy distillate fraction is included in the vacuum bottoms slurry.

5. A method according to claim 3 wherein the conversion of carbon monoxide and hydrogen to methanol is incomplete, and the uncovered carbon monoxide and hydrogen are burned for the generation of electric power.

6. A method according to claim 3 where the amount of gasifier feed slurry is increased by admixing coal therewith.

7. A method according to claim 6 where the gasifier feed is up to 30% coal (by weight).

8. A method according to claim 1 where said carbon monoxide and hydrogen are converted to methane.

* * * * *